US008522774B2

(12) United States Patent
Zambon et al.

(10) Patent No.: US 8,522,774 B2
(45) Date of Patent: Sep. 3, 2013

(54) AEROSOL APPARATUS, IN PARTICULAR FOR CHILDREN

(75) Inventors: Elena Zambon, Milan (IT); Gianluca Basso, Bresso (IT)

(73) Assignee: Zambon S.p.A., Bresso (IT)

( * ) Notice: Subject to any disclaimer, the term of this patent is extended or adjusted under 35 U.S.C. 154(b) by 1213 days.

(21) Appl. No.: 11/761,824

(22) Filed: Jun. 12, 2007

(65) Prior Publication Data

US 2008/0078381 A1 Apr. 3, 2008

(30) Foreign Application Priority Data

Sep. 29, 2006 (EP) .................................... 06425670

(51) Int. Cl.
*A61M 11/00* (2006.01)
(52) U.S. Cl.
USPC ............. 128/200.14; 128/200.24; 128/206.21
(58) Field of Classification Search
USPC ............. 128/200.14, 200.24, 202.22, 206.21, 128/206.28
See application file for complete search history.

(56) References Cited

U.S. PATENT DOCUMENTS

| | | | | |
|---|---|---|---|---|
| 4,257,415 A | * | 3/1981 | Rubin ....................... | 128/200.21 |
| 5,333,106 A | * | 7/1994 | Lanpher et al. ............... | 600/538 |
| 5,992,155 A | * | 11/1999 | Kobayashi et al. ............... | 62/3.7 |
| 6,442,018 B1 | | 8/2002 | Dinkin | |
| 6,752,145 B1 | * | 6/2004 | Bonney et al. ............ | 128/200.23 |
| 6,932,083 B2 | * | 8/2005 | Jones et al. ............... | 128/200.23 |
| 6,962,151 B1 | | 11/2005 | Knoch et al. | |
| 2003/0101178 A1 | * | 5/2003 | Miyata et al. ...................... | 707/6 |
| 2004/0084045 A1 | * | 5/2004 | Ziegler et al. ............ | 128/200.23 |
| 2004/0210151 A1 | | 10/2004 | Tsukashima et al. | |
| 2005/0117292 A1 | * | 6/2005 | DiFonzo et al. ............... | 361/687 |
| 2005/0218172 A1 | * | 10/2005 | Hassett .......................... | 224/585 |
| 2005/0231835 A1 | * | 10/2005 | Tokushita et al. ............. | 359/871 |
| 2006/0253045 A1 | * | 11/2006 | Coifman ....................... | 600/538 |
| 2009/0223513 A1 | * | 9/2009 | Papania et al. ........... | 128/200.16 |

FOREIGN PATENT DOCUMENTS

EP 0 667 168 A1 8/1995

* cited by examiner

*Primary Examiner* — Justine Yu
*Assistant Examiner* — Colin W Stuart
(74) *Attorney, Agent, or Firm* — Oblon, Spivak, McClelland, Maier & Neustadt, L.L.P.

(57) ABSTRACT

An aerosol apparatus including a nebulizer device and a mask suitable for receiving a substance substantially in the sol state from the nebulizer device is described. The apparatus also includes a display device able to display a sequence of images to a patient while he/she is using the apparatus. The display device may be a DVD player which conveniently is able to be separated from the aerosol apparatus. The apparatus is particularly suitable for use by patients who are children.

17 Claims, 2 Drawing Sheets

AEROSOL APPARATUS, IN PARTICULAR FOR CHILDREN

Figure 1:
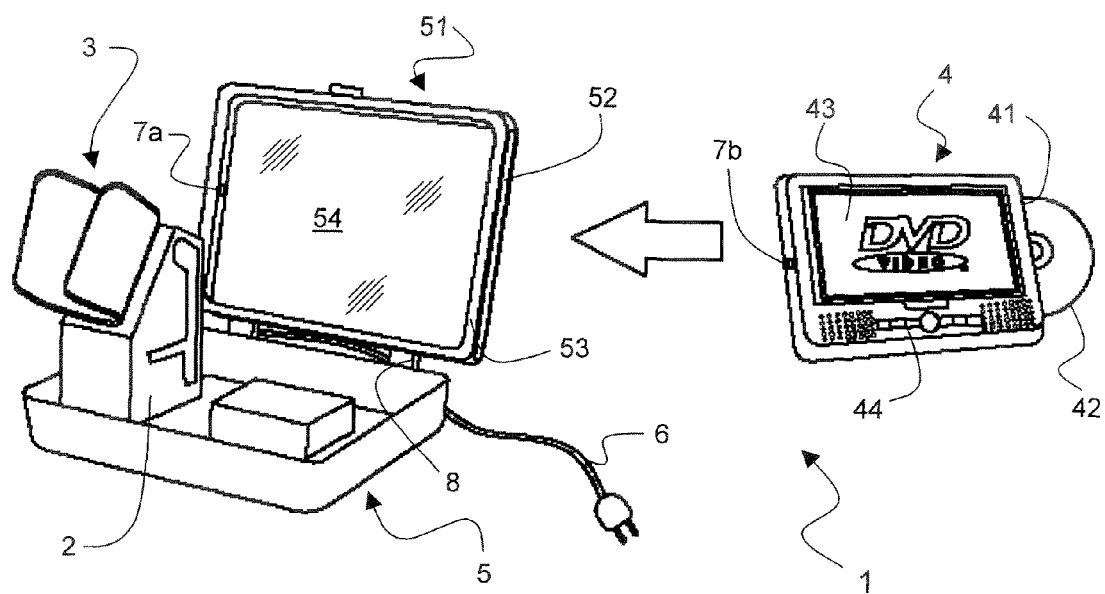

The present invention relates to an aerosol apparatus for administering a substance (typically a medicinal substance) by means of inhalation, in particular (but not exclusively) to a child.

It is known that the inhalation of air in which curative substances are dispersed has a therapeutic effect on infections of the respiratory apparatus. In addition to natural nebulization sources (for example, standing close to the sea allows one to breathe iodine which is nebulized by breaking of the waves) fairly basic nebulization methods such as vapour inhalations are known. Aerosol nebulization apparatus, or, in short, aerosol apparatus, are also known.

An aerosol apparatus allows the introduction, into the respiratory apparatus, by means of inhalation, of a substance (typically a medicinal substance) in the "sol" state for therapeutic purposes. The "sol" state is the state of a material which is midway between that of a liquid and gas. In other words, the particles which form it are not as dispersed as those of a gas, but are also not as concentrated as those of a liquid substance.

Aerosol nebulization is a therapeutic technique which is very advantageous because it favours the administration, within the respiratory tract, of drugs which may exercise their pharmacological effect in situ.

Aerosol apparatus of the mechanical (or pneumatic) type are known. They consist of a membrane or piston compressor and an actual nebulizer. Nebulization is obtained by means of the Venturi effect: the compressor produces an air flow at a high pressure and high speed which is forced onto the end of a sample vessel containing the medicinal substance. The liquid is then "atomized" into particles which may be inhaled through the mouth or nose, or both, by means of a special mask.

Ultrasound aerosol apparatus in which nebulization is achieved by means of a piezoelectric effect are also known: a transducer emanates electromagnet waves of the ultrasound type which fragment the medicinal solution.

Whatever the type of aerosol apparatus used, the methods of performing the aerosol therapy in order to achieve a good therapeutic result are very important. For the same amount of medicinal substance inhaled, the effectiveness of the aerosol therapy depends essentially on the length of time during which the patient undergoes therapy and the respiration frequency. In other words, treatment by means of aerosol therapy is particularly effective if the patient inhales the medicinal substance in the sol state for a period of about 15-20 minutes (or also more) and if inhalation is performed breathing deeply and at regular intervals.

However, many patients do not willingly undergo aerosol therapy sessions and, of their own initiative, tend to reduce the inhalation times, i.e. very often the patients interrupt inhalation before the end of the predefined time period considered to be optimal. Moreover, some patients tend to experience negatively or are even anxious about the aerosol therapy session. This causes them to breathe in an irregular, fast and superficial manner.

In all cases, the reduction in the time and the irregular breathing do not allow optimum therapeutic results to be obtained.

The abovementioned problems generally arise more frequently in the case of patients who are children. It has been noted, in this connection, that more than 50% of the patients who are children perform aerosol therapy incorrectly and discontinuously, resulting in no beneficial therapeutic effect.

Young patients are often unable to understand the benefits which can be achieved with an aerosol therapy session and do not willingly agree to use an aerosol apparatus. In the case of very young children it is not even possible to convince them that it is better to take deep breaths and to remain wearing the mask for a certain predetermined period of time.

Various manufacturers of aerosol apparatus, in an attempt to solve at least partly the abovementioned problems, aim to provide apparatus which are able to perform increasingly shorter aerosol therapy cycles.

U.S. Pat. No. 6,962,151 describes an electronic nebulizer which allows the therapy period to be reduced considerably to about three minutes.

The Applicant has faced the abovementioned problems in an attempt to provide an aerosol apparatus which is able to ensure more effective therapy.

The Applicant has found that the primary factors which make an aerosol therapy treatment effective are the frequency and the intensity of breathing. The Applicant has also noted that said factors, in turn, depend on the state of agitation or relaxation of the patient: a person who is anxious and not relaxed takes short quick breaths at relatively frequent intervals; on the other hand, a relaxed patient generally breathes more deeply and at a slower rate. The latter is a preferable condition for performing aerosol therapy.

Another factor considered to be important for the purposes of obtaining the improved benefits from an aerosol therapy session is the need to keep the patient's face in contact with the inhalation mask. If the patient moves his/her mouth and/or his/her nose away from the mask, the substance in the sol state is mixed with air and results in "dilution" of the inhaled substance, in addition to cooling and condensation.

The object of the present invention is therefore to provide an aerosol apparatus which solves the abovementioned problems and in particular ensures that the patient is in the best psychological and physical condition to undergo aerosol therapy, resulting in completely effective treatment.

This object, together with others, is achieved by an apparatus having the characteristic features of Claim 1. Further advantageous characteristics of the invention are contained in the dependent claims.

The aerosol apparatus according to the invention comprises a nebulizer device and a mask suitable for receiving a substance substantially in the sol state from the nebulizer device. It also comprises a display device able to display a sequence of images to a patient while he/she is using the apparatus.

The display device may comprise an optical or magnetic medium player. In a preferred embodiment, the display device comprises a DVD (Digital Versatile Disc) player.

The display device comprises a display or monitor which may be a liquid crystal display (LCD) or a plasma screen.

Advantageously, the display device is of the type with side loading of the DVDs.

The display device may comprise means for emitting sounds associated with the images displayed.

Advantageously a case-like container is envisaged for storing and transporting at least the nebulizer device and the mask. The case-like container, in turn, may comprise a lid designed to house at least part of the display device. The lid is provided with a slit having dimensions suitable for being able to introduce the display device inside it.

Preferably, the mask is shaped so that the vapour emitted does not disturb viewing of the images of the display device.

An advantage of the invention is that the display device may be able to be separated from the apparatus so that it is possible to use it separately.

Figure 2:
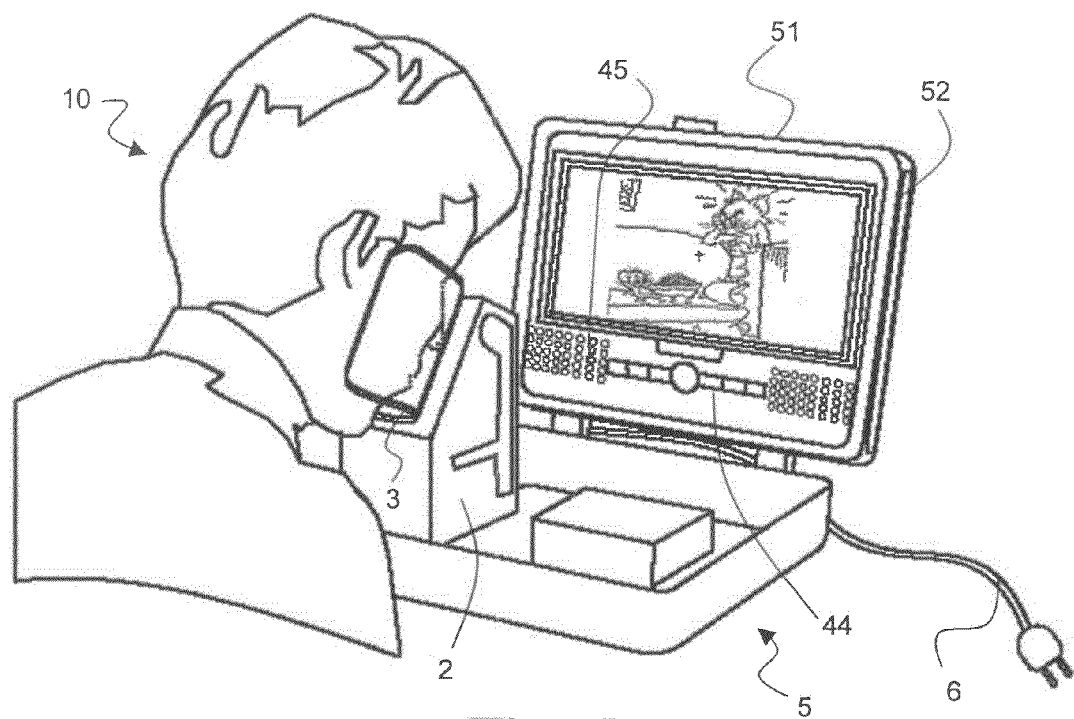

The apparatus advantageously is suitable for use by children. A detailed description of the invention now follows, being provided solely by way of a non-limiting example, to be read with reference to the accompanying figures in which:

FIG. 1 shows in schematic form an aerosol apparatus according to an embodiment of the invention, while it is being prepared for use; and FIG. 2 shows in schematic form the aerosol apparatus according to FIG. 1 during use.

An aerosol apparatus 1 according to an embodiment of the present invention is schematically shown in FIG. 1. The apparatus 1 comprises a nebulizer device 2 and a mask 3. The nebulizer device 2 may be equally well of the mechanical, pneumatic, ultrasound or any other type. The mask 3 is connected to the nebulizer device 2 so as to receive a substance (for example a medicinal substance) substantially in the sol state. During use, the mask 3 is moved towards the mouth and/or the nose of the patient 10 who is thus able to inhale the substance which is typically for therapeutic purposes.

According to the present invention, the apparatus 1 also comprises a display device 4 which allows sequential viewing of images, i.e. a succession of one or more static and/or moving images. The multimedia display device 4 may comprise a monitor of a computer (typically a portable computer), mobile phone (for example smart phone), so-called palm-top computer or the like. The display device 4 may conveniently comprise a television monitor. Even more preferably, the display device 4 may comprise a player (and/or recorder) of magnetic and/or optical media such as a DVD or video CD or videocassette player (and/or recorder).

In an advantageous embodiment, the display device 4 comprises a DVD player 41. In another advantageous embodiment, the display device 4 comprises a monitor of a personal computer or the like for displaying educational games or the like.

Typically, the display device 4 comprises means for emitting sounds associated with the images displayed. Therefore, for example, in the case where a film or a cartoon is shown, the images will be accompanied by the corresponding audio or sound signals.

In addition or as an alternative to the abovementioned sound emitting means, the display device 4 may comprise means for displaying writing associated with the images shown. Therefore, for example, in the case where a film or a cartoon is shown, the images will be accompanied by subtitles. This function is useful for users who are deaf or have impaired hearing or when it is required to avoid disturbing people who are in the vicinity of the aerosol apparatus 1 (but not involved in the therapy). This function is also useful where the audio associated with the images is in a language different from the native tongue of the user. In this case, the therapy session could also be used to learn a new language.

According to an advantageous embodiment, the DVD player 41 is of the type with slot-in (lateral) loading of the DVD discs 42. This type of player, as opposed to players with a hinged opening system, is formed by a single body of the parallelepiped type which is relatively thin (currently, for example, in the region of a few centimeters). A slot for inserting the discs is provided on the side of the parallelepiped body. A display monitor 43 is instead present on a face of the player. Operating keys 44 may also be provided laterally or on the face of the monitor 43. The abovementioned sound-emitting means 45 (typically associated with the images displayed) may also be provided laterally or on the face of the monitor.

By way of example, the monitor 43 may be conveniently of the LCD or plasma type. A size for the monitor 43 which is considered suitable for the purpose is 7" with a side ratio of 16:9. Obviously, monitors with greater or smaller dimensions, if necessary with a different side ratio, may also be used.

According to an advantageous embodiment of the invention, the apparatus 1 comprises a case-like container 5 for storing and transporting at least the nebulizer device 2 and the mask 3. The case-like container has a closed bottom, side walls and a lid 51 which may also be closed. The lid 51 is hinged on a side wall (typically on the rear side wall). The lid may also be designed to house the display monitor 43. For example, a slit 54 with a size such that the display monitor 43 may be inserted inside it (for example the DVD player 41) may be envisaged.

The slit 54 is conveniently provided on one side, taking into account, if necessary, the need to have access to the disc insertion slot so as to be able to introduce/extract easily a disc 42 into/from the player 41 when the latter is inserted inside the slit 54 and is substantially housed inside the lid 51 of the container 5.

The slit is conveniently delimited by the outer surface 52 of the lid 51 and by an inner rim 53. The rim 53 defines a window with dimensions preferably at least equal to the dimensions of the monitor 43. Preferably, if the controls 44 of the display device 4 are situated on the front, the dimensions of the rim 53 must not prevent access to the controls 44.

Fixing means 7*a* and 7*b* are envisaged for preventing the possibility of the display monitor 43 inadvertently and involuntarily coming out of the slit 54.

The display device 4 may, if necessary, be extracted from the slit 54 which houses it so as to be able to use it independently of the nebulizer device 2. In other words, the display device 4 (for example the DVD player 41) may also be used when the nebulizer device 2 is not used.

The display device 4 may be powered by a battery, for example a rechargeable lithium battery and/or by a separate electric power supply and/or by the same electric power supply 6 which powers the nebulizer device 2. This latter advantageous possibility may be provided by envisaging a system of electrical contacts (or if necessary a plug and socket system) between the lid 51 and the display device 4. The electric power is conveyed to the lid 51, for example via the hinges 8, in the same way as in a portable computer.

The distance and the inclination of the display device 4 are critical for the invention. They are preferably calculated depending on the inhalation mask 3 so that the best view of the images shown on the monitor 43 is obtained when the patient's face is kept properly in contact with the mask 3. In other words, the position, distance and inclination of the monitor 43 are a consequence of the position and the shape of the mask 3. The patient 10 will not be encouraged to change position because this would worsen the view of the images shown on the monitor 43.

The aerosol apparatus 1 has proved to be particularly effective when used for aerosol therapy carried out on a group of children. During inhalation cartoons were shown. All the children undergoing therapy reacted positively to the said therapy, maintaining without difficulty a correct position for the entire duration (about 15 to 20 minutes) of each single treatment cycle. For this purpose, the duration of the cartoons sequences shown was specially selected according to the duration of the treatment cycle. The degree of relaxation of the patients was calculated as a function of the frequency of closing of the eyelids (number of eye blinks per minute). A substantial reduction in the frequency of closing of the eyelids in patients concentrating on watching the images shown on the monitor was noted. It is considered that this state of relaxation was decisive in ensuring the effectiveness of the therapy, having positively influenced the patients' breathing.

The invention claimed is:

1. An aerosol apparatus comprising:
a nebulizer device;
a mask that receives a substance substantially in a sol state from the nebulizer device;

a display device configured to display a sequence of images to a patient while the patient uses the apparatus; and a case, wherein the nebulizer device and the mask are configured to be stored and transported in the case, and the nebulizer device is configured to stand on a bottom of the case and to hold the mask that is connectable to the nebulizer device above the bottom without any support by the patient so the display device is viewable to the patient while the patient uses the apparatus, wherein the mask is connectable to a surface of the nebulizer device that is inclined relative to the bottom of the case, and the surface of the nebulizer device that is inclined relative to the bottom of the case abuts a second surface of the nebulizer device that is downwardly inclined toward the display device, wherein the entire display device fits within a lid of the case, and wherein the display device is removably affixed to the case.

2. The apparatus according to claim 1, wherein said display device includes an optical or magnetic medium player.

3. The apparatus according to claim 1, wherein said display device includes a digital versatile disc (DVD) player or a monitor of a personal computer.

4. The apparatus according to claim 1, wherein said display device includes a display or monitor including a liquid crystal display (LCD) or a plasma screen.

5. The apparatus according to claim 3, wherein said display device includes side loading of digital versatile discs (DVDs).

6. The apparatus according to claim 1, wherein said display device emits sounds associated with the images displayed.

7. The apparatus according to claim 1, wherein said lid includes a slit configured to hold the display device inside thereof.

8. The apparatus according to claim 1, wherein the mask is shaped so that a vapour emitted does not disturb viewing of the images of the display device.

9. The apparatus according to claim 1, wherein said display device is separable from the apparatus so that the display device can be used separately.

10. The apparatus according to claim 1, wherein said patient is a child.

11. The apparatus according to claim 2, wherein said display device includes a digital versatile disc (DVD) player or a monitor of a personal computer.

12. The apparatus according to claim 1, wherein the display device is positioned to provide a view of the images shown on the display device to a patient using the apparatus.

13. The apparatus according to claim 1, wherein the display device is positioned at a specific inclination and distance with respect to the mask to provide a view of the images shown on the display device to a patient when the patient's face is properly in contact with the mask.

14. The apparatus according to claim 1, wherein the case includes a fixing device to prevent the display device from coming out of the case.

15. The apparatus according to claim 1, wherein the case includes a hinge to pivotably attach the lid to the case.

16. The apparatus according to claim 15, further comprising:

an electrical contact on the lid between the lid and the display device to supply power to the display device, wherein power is conveyed to the electrical contact via the hinge.

17. An aerosol apparatus comprising:

means for nebulizing;

means for receiving a substance substantially in a sol state from the means for nebulizing;

means for displaying a sequence of images to a patient while the patient uses the apparatus; and means for storing, wherein the means for nebulizing and the means for receiving are configured to be stored and transported in the means for storing, and the means for nebulizing is configured to stand on a bottom of the means for storing and to hold the means for receiving that is connectable to the means for nebulizing above the bottom without any support by the patient so the means for displaying is viewable to the patient while the patient uses the apparatus, wherein the means for receiving is connectable to a surface of the means for nebulizing that is inclined relative to the bottom of the means for storing, and the surface of the means for nebulizing that is inclined relative to the bottom of the means for storing abuts a second surface of the means for nebulizing that is downwardly inclined toward the means for displaying, wherein the entire means for displaying fits within a lid of the means for storing, and wherein the means for displaying is removably affixed to the means for storing.

* * * * *